(12) United States Patent
Karasina

(10) Patent No.: US 10,835,032 B2
(45) Date of Patent: Nov. 17, 2020

(54) ILLUMINATED SURGICAL UTILITY TABLE

(71) Applicant: Svetlana Karasina, Basking Ridge, NJ (US)

(72) Inventor: Svetlana Karasina, Basking Ridge, NJ (US)

(*) Notice: Subject to any disclaimer, the term of this patent is extended or adjusted under 35 U.S.C. 154(b) by 0 days.

(21) Appl. No.: 14/539,949

(22) Filed: Nov. 12, 2014

(65) Prior Publication Data
US 2016/0128465 A1    May 12, 2016

Related U.S. Application Data

(60) Provisional application No. 61/903,242, filed on Nov. 12, 2013.

(51) Int. Cl.
| | |
|---|---|
| A47B 13/12 | (2006.01) |
| A47B 13/00 | (2006.01) |
| F21V 23/04 | (2006.01) |
| A61B 50/33 | (2016.01) |
| A61B 50/10 | (2016.01) |
| A61B 50/15 | (2016.01) |
| A61B 50/24 | (2016.01) |
| A61B 50/13 | (2016.01) |

(52) U.S. Cl.
CPC .......... A47B 13/12 (2013.01); A47B 13/003 (2013.01); A61B 50/10 (2016.02); A61B 50/15 (2016.02); A61B 50/33 (2016.02); F21V 23/0471 (2013.01); F21V 23/0485 (2013.01); A47B 2220/0077 (2013.01); A61B 50/13 (2016.02); A61B 50/24 (2016.02)

(58) Field of Classification Search
CPC ............ F21V 23/0471; F21V 23/0485; A61B 19/0248; A61B 19/026; A61B 19/52; A61B 2019/0255; A61B 2019/0259; A47B 13/003; A47B 13/12; A47B 2220/0075; A47B 2220/0077
See application file for complete search history.

(56) References Cited

U.S. PATENT DOCUMENTS

| | | | | |
|---|---|---|---|---|
| 3,422,774 A | * | 1/1969 | Hagans ................ | A47B 13/12 108/23 |
| 4,927,214 A | * | 5/1990 | Kaufman ........... | A61B 19/0248 108/159 |
| 5,605,393 A | * | 2/1997 | Cucchi .................... | A61D 3/00 108/23 |
| 6,715,956 B1 | * | 4/2004 | Weber ...................... | E01C 5/20 404/18 |
| 2006/0244593 A1 | * | 11/2006 | Nycz ..................... | A61F 2/4425 340/572.1 |

(Continued)

FOREIGN PATENT DOCUMENTS

FR          2749926 A1 * 12/1997 ............. A47B 13/12

*Primary Examiner* — Alexander K Garlen
(74) *Attorney, Agent, or Firm* — Margaret LaCroix

(57) ABSTRACT

Accordingly, on one aspect, an illuminated utility table is provided that includes: a planar table top having a horizontal surface for a package of wrapped instruments to be placed thereon, wherein the table top is at least one of transparent and translucent; a table frame, wherein the table top is removably coupled to the table frame; and a light source, wherein the light source is coupled to the table and configured to shine light vertically upward through the table top for inspection of the package wrapped placed on the table top.

11 Claims, 2 Drawing Sheets

(56) References Cited

U.S. PATENT DOCUMENTS

| | | | | |
|---|---|---|---|---|
| 2008/0291659 A1* | 11/2008 | Huang | ............... | A47B 13/12 |
| | | | | 362/84 |
| 2009/0045154 A1* | 2/2009 | Gerstner | ........... | A61B 19/0256 |
| | | | | 211/126.15 |
| 2015/0031960 A1* | 1/2015 | Cohen | ............... | A61B 19/0248 |
| | | | | 600/249 |

* cited by examiner

ILLUMINATED SURGICAL UTILITY TABLE

RELATED APPLICATION

This application claims the benefit of U.S. (Provisional) Application No. 61/903,242, filed Nov. 12, 2013, which is hereby incorporated herein by reference.

BACKGROUND OF THE INVENTION

The present application related to tables and more particularly illuminated surgical utility tables.

In accordance with Association of Perioperative Registered Nurses (AORN) Perioperative Standards and Recommended Practices 2013, the following are recommended for maintaining a sterile field:

Recommendation I—Sterile drapes should be handled as little as possible. Rapid movement of draping material creates air currents on which dust, lint, and other particles can migrate.

Recommendation II—Items within the sterile field should be sterile. To ensure that only sterile items are presented to the sterile field, all items should be inspected immediately before presentation to the field for proper packaging.

Recommendation III—Movement of personnel should be kept to a minimum while invasive and noninvasive procedures are in progress. Careful assessment of the patient and planning for patient care needs should reduce the need for excessive movement and activity during the procedure. Air is a potential source of microorganisms that can contaminate surgical wounds. Because microbial shedding increases with activity, greater amounts of airborne contamination can be expected with increased movement of surgical team members. Traffic in an out of the operating room (OR) should be minimized by preplanning so that turbulence from this activity is minimized during the procedure or when sterile supplies are opened.

Recommendation IV—Surgical Site Infections are a leading cause of patient morbidity and mortality in the United States (average 500,000 occurrences a year). Rigorous adherence to the principles of asepsis is the foundation of surgical site prevention and should never be circumvented to save time or money. A sterile field should be prepared and maintained for every surgical patient.

Recommendation V—Scrubbed personnel should keep their arms and hands above level of their waists at all times. Hands should remain in front of the body above waist level so the hands remain visible. Contamination may occur when arms and hands are moved below waist level.

Recommendation VI—The end user should visually inspect the package or container before opening for package integrity (e.g., free of holes in the fabric/paper, effective seal in containers).

Currently, many surgical trays with instruments are wrapped in sterile wrappings that need to be opened before surgery. Upon opening of the surgical trays, the sterile wrapping has to be checked for damages (e.g., holes) that compromise the sterility. In other words, in present time, nursing staff checks for holes in the wrapping by lifting the wrapping up to the ceiling lights, which causes significant air currents in the OR. Accordingly, there is a need for devices and methods for checking sterile wrappings for damage with a significant reduction of the air currents in operating room.

SUMMARY OF THE INVENTION

The present application is directed to devices and methods for checking sterile wrappings for damage, such as holes, which generally produce fewer air currents in relation to conventional methods for doing so. That is, the devices and methods disclosed herein provide a way for the easy detection of damaged sterile wrappings that involve fewer air current generating activities. Doing so reduce the risk of Surgical Site Infection as a result of air-born contaminants and may decrease instances of the use of instruments contaminated as a result of damaged wrappings.

Accordingly, on one aspect, an illuminated utility table is provided that includes: a planar table top having a horizontal surface for a package of wrapped instruments to be placed thereon, wherein the table top is at least one of transparent and translucent; a table frame, wherein the table top is coupled to the table frame; and a light source, wherein the light source is coupled to the table and configured to shine light vertically upward through the table top for inspection of the package wrapped placed on the table top.

In at least one embodiment, the light source provides sufficient illumination to inspect a plurality of layers of wrapping for holes.

In at least one embodiment, a power source electrically coupled to the light source to supply power to the light source.

In at least one embodiment, the power source comprises a rechargeable battery located within the table frame.

In at least one embodiment, the table includes a switch for selectively turning the light source on and off.

In at least one embodiment, the switch is a pressure activated switch coupled to the table top so as to turn the light source on upon detection of the package placed on the table top.

In at least one embodiment, the table frame has a sealed space therein and wherein the light source, power, and the light switch are located within the space.

In at least one embodiment, the space has a plurality of panels enclosing the space, including a translucent or transparent top panel essentially parallel to the table top, and wherein the light source shines light through both the tap panel and the table top.

In at least one embodiment, the table top includes one or more structures that engage corresponding structure on the table frame to arrest horizontal movement between the table top and the table frame.

In at least one embodiment, the structures allow vertical movement between the table top and the table frame.

In at least one embodiment, the table top comprises at least one of male structures and female structures that engage corresponding structure in the table frame.

Additional aspects of the present invention will be apparent in view of the description which follows.

DETAILED DESCRIPTION OF THE INVENTION

The present application provides devices and corresponding methods of using the devices for checking sterile wrappings for damage, such as for holes, which involve fewer air current generating activities in comparison to conventional methods.

Figure 1:
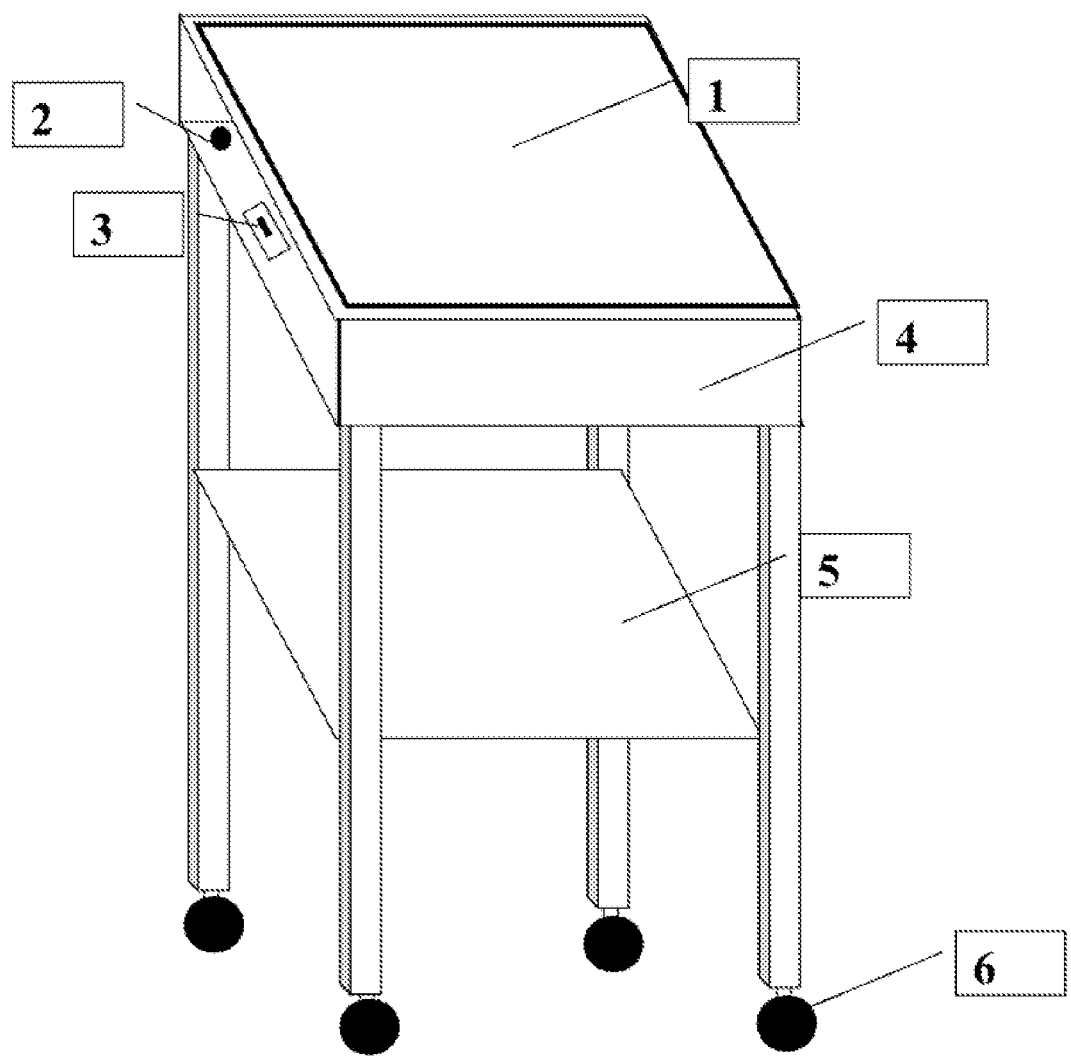
FIG. 1 is a perspective view of an illuminated utility table according to one embodiment of the tables disclosed herein.
Figure 2:
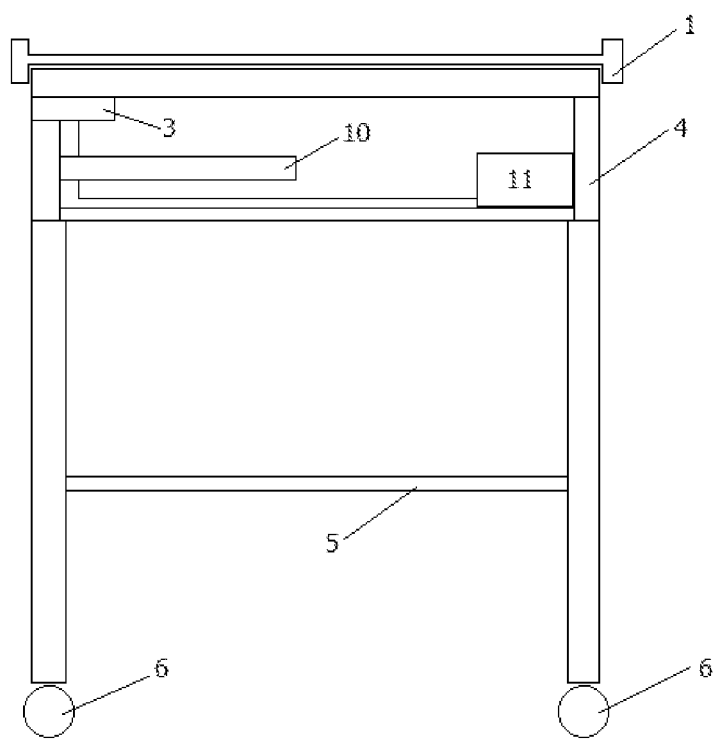
FIG. 2 shows a cross-sectional view of the illuminated utility table according to one embodiment of the tabled disclosed herein.

Referring to FIGS. 1-2, in at least one embodiment, an illuminated utility table is provided that includes a table top (1) coupled to an illuminated table frame (4). The table top (1) is a planar structure with a horizontal surface for medical personnel to place wrapped sterilized instruments and/or wrapping thereon for inspection and use. That is, the wrapped surgical instruments may be placed on the table top (1), the wrapping undone according to established procedures, the instruments and the wrapping inspected, and the instruments removed from the wrapping for use. The instruments may be placed onto another table, such as an instrument table, once inspected.

The inspection process may be facilitated by providing a utility table with a light source (10) so that personnel are not required to remove the wrapping from the table top (1) for inspection once the wrapping is undone. That is, personnel no longer have to raise the wrapping to the ceiling light to visually inspect the wrapping for holes. In this regard, the illuminated surgical utility table, e.g., the table frame (4), has a light source (10) situated within the table frame (4) in such a way that it shines light vertically upward through the table top (1). It is to be understood that in addition to the light source (10), the illuminated surgical utility table may be equipped with an additional light source (not shown) on the side of the table frame (4) such that the additional light source illuminates the object placed on the table top (1) from at least one additional side besides the light source (10).

The table top (1) is preferably made from a transparent or translucent material, such as glass, tempered glass, etc., and the light from the source (10) illuminates upward directly or indirectly through the table top (1), which allows personnel to inspect wrapped and unwrapped packages placed onto the table top (1) for holes in situ. The transparent or translucent material should be able to hold more than 80 lbs of force placed thereon. It can be appreciated that this significantly limits the number of movements necessary to properly inspect wrapping for holes. That is, being able to inspect instrument wrapping without having to move the instrument package excessively reduces air currents that would otherwise be created that could carry contaminants therein.

The configuration noted herein may be achieved in a variety of ways. In at least one embodiment, the illuminated table includes a table top (1), a optional hole (2) in the side of the table frame (4), which may be used to pass a power cord, or pneumatic or other tube, a light switch (3), e.g., on a left panel, with a light or lights immediately behind the left panel, the table frame (4), an optionally removable lower shelf (5), and optional casters (6). The lights preferably provide sufficient illumination for the visual inspection of one or more layers of wrapping for holes.

On this table top (1) are set wrapped sterilized instruments. Underneath the glass is an enclosed space having a with a floor, optionally enclosed by a left and optional front, rear, and right sides, and holding a light (such as, a light emitting diode, fluorescent light, incandescent light, etc.) to illuminate the instruments and/or the wrapping on the transparent/translucent table top (1). The enclosed space may hold an optional battery (11) to power the light (the other way of powering it being by a cord from the light to a wall outlet), which can be seen through the table top (1) by surgical personnel.

In one embodiment, on one side of the enclosed space is a switch (3) for turning the light located along an inner edge of the enclosed space on and off so as to illuminate the wrapped instruments. The panel on the left may also have an optional hole (2) through which may pass an electric cord to power the light (in case a battery is not used) or another tube.

In another embodiment, the switch (3) is a pressure-activated sensor-switch positioned within the table frame and is adjacently connected to the table top (1) such that light source (11) is activated to shine the light through the table top (1) when the switch (3) detects pressure of physical weight of wrapped instruments being placed on a surface of the table top (1). Having a pressure-activated sensor-switch allows to further limits the number of movements necessary to properly inspect wrapping for holes.

In an embodiment, the light source is fed by electrical current received through a cord connected to an external power source (e.g., electrical outlet in the OR). Alternatively, the light source is fed by electrical current received from a battery pack (11) positioned within the table frame (4). It is to be understood that the battery pack can be a rechargeable battery pack (11) having a plug element positioned on the outer surface of the table frame replacing the hole (2) such that the rechargeable battery pack (11) could be recharged regularly. The battery pack (11) can also be a replaceable battery pack (11). Having a replaceable battery pack (11) will allow to eliminate the need in having the hole (2) further limiting a number of inner surfaces of the table frame on which microorganisms and dust can accumulate.

It is to be understood that other objects may be stored in the space immediately below the top, due to the bottom of the space parallel to the table top. Partially down from top is an optional shelf (5) also parallel to the table top on which may be placed other objects. An optional and recommended caster (6) appears on the bottom of each table leg.

The space may be sealed to ease in disinfection of the table. In this regard, the enclosed space has left, right, front and back sides, as well as a bottom parallel to the table top (1) and a top that is also transparent or translucent. In this regard, the light shines through the top of the enclosed space and the table top (1).

The mechanism for attaching the table top (1) to the table frame (4) may vary. In one embodiment, the table top (1) includes one or a plurality of structures that engage into corresponding structures in the frame. For example, the table top (1) may include a plurality of male structures, such as pegs, that fit into corresponding female structures within the frame (4) to arrest horizontal movement of the table top (1) relative to the frame (4). The pegs may be located, for example, at each corner of a rectangular top. The structures may also be reversed. That is, the pegs may be part of the table frame (4), which fit into recesses in the table top (1). Moreover, the table top (1) bottom (facing the top of the enclosed space) may include a lip around the perimeter of the table top. This lip may be dimensioned so that the lip engages the perimeter of the enclosed space. In other words, the lip forms the female structure and the top of the enclosed space forms the male structure. In this regard, the top of the enclosure fits within the perimeter lip of the top (1) so as to arrest horizontal movement of the table top (1). The table top (1) may also include a lip on a top of the table top (1) opposite the bottom to prevent instruments from falling of the edges. In this instance, the table top (1) may have a cross section perpendicular to the planer top and bottom surfaces of the table top (1) that resembles the letter H. This H-shaped cross section may be characteristic of all such cross sections of the table top (1). The enclosed space may also have a lip extending vertically upward from the top surface of the enclosed space to form a recess wherein the table top (1) may be fit into. The preferable size of this table is about 22"×15.5"×35" tall. The table is scalable, thus not being restricted to the specific sizes mentioned above. The table may be made of any materials and may be shaped in any way, as long as the scope, purpose, and functionality are maintained.

The table may be used as follows: One merely lays wrapped surgical instruments on the transparent/translucent table top (1) through which shines a light from below and illuminated the wrapping for convenient and effective examination of the wrapping for holes and other damages. The wrapping may be undone upon initial confirmation and the wrapping inspected further. This table may be used in any surgical environment, such as an operating room, hospital emergency room, Labor and Delivery Department, Radiology Department—for non invasive surgery, or in any other environment which there is a need to examine items with the aid of an illuminated table top.

While the foregoing invention has been described in some detail for purposes of clarity and understanding, it will be appreciated by one skilled in the art, from a reading of the disclosure, that various changes in form and detail can be made without departing from the true scope of the invention.

What is claimed is:

1. An illuminated utility table for checking sterile wrappings for damage to decrease air currents, comprising:
    a planar table top having a horizontal surface, wherein the table top is made of a tempered glass capable of holding at least 80 pounds thereon and is transparent;
    a table frame, wherein the table top is removably coupled to the table frame, the table frame having an enclosed sealed space formed from left, right, front and back sides, a bottom and a planar top panel parallel to the table top, wherein the table top abuts and rests on said top panel, and said top panel is translucent so that flight shines through the top panel of the enclosed sealed space and the table top, wherein the table top includes structures that allow vertical movement and arrest horizontal movement while coupled to and slid across the table frame;
    a light source, wherein the light source is coupled to the table and configured to shine the light vertically upward through the table top; and
    a switch for selectively turning the light source on and off, wherein the switch is a pressure-activated sensor-switch positioned within the table frame and adjacently connected to the table top such that the light source is activated to shine the light through the table top when the switch detects pressure of physical weight of an item placed on the table top.

2. The table of claim 1, wherein the light source provides sufficient illumination of the item placed on the table top.

3. The table of claim 1, comprising a power source electrically coupled to the light source to supply power to the light source.

4. The table of claim 3, wherein the power source comprises a rechargeable battery located within the table frame.

5. The table of claim 1, wherein the light source, a power source, and the light switch are located within the sealed space.

6. The table of claim 1, wherein the table top comprises at least one of male structures and female structures that engage corresponding structure in the table frame.

7. The table of claim 1, wherein the table top has left, right, front and back sides and said table top has a cross section perpendicular to a top and bottom surface of the table top on both the front and back sides so that the table top resembles the letter H.

8. An illuminated utility table for checking sterile wrappings for damage to decrease air currents, comprising:
    a planar table top having a horizontal surface, wherein the table top is made of a tempered glass capable of holding at least 80 pounds and is transparent;
    a table frame, wherein the table top is removably coupled to the table frame, the table frame having an enclosed sealed space formed from left, right, front and back sides, a bottom and a planar top panel parallel to the table top, wherein the table top abuts and rests on said top panel, and said top panel is translucent so that light shines through the top panel of the enclosed sealed space and the table top, wherein the table top has an H-shaped cross section and includes structures that allow vertical movement and arrest horizontal movement while coupled to and slid across the table frame;
    a light source, wherein the light source is coupled to the table and configured to shine the light vertically upward through the table top; and
    a switch for selectively turning the light source on and off, wherein the switch is a pressure-activated sensor-switch positioned within the table frame and adjacently connected to the table top such that the light source is activated to shine the light through the table top upon detection of pressure of physical weight of an item placed on the table top.

9. The table of claim 8, wherein the light source, power, and the light switch are located within the space.

10. The table of claim 8, wherein the table top comprises at least one of male structures and female structures that engage corresponding structure in the table frame.

11. An illuminated utility table for checking sterile wrappings for damage to decrease air currents, comprising:
    a planar table top having a horizontal surface, wherein the table top is made of a tempered glass capable of holding at least 80 pounds and is at least one of transparent or translucent;
    a table frame, wherein the table top is coupled to the table frame, the table frame having an enclosed sealed space formed from left, right, front and back sides, a bottom and a planar top panel parallel to the table top, wherein the table top abuts and rests on said top panel, and said top panel is translucent so that flight shines through the top panel of the enclosed sealed space and the table top, wherein the table top includes structures that allow vertical movement and arrest horizontal movement while coupled to and slid across the table frame;
    a light source, wherein the light source is coupled to the table and configured to shine the light vertically upward through the table top; and
    a switch for selectively turning the light source on and off.

* * * * *